(12) United States Patent
Sabovic et al.

(10) Patent No.: US 10,281,744 B2
(45) Date of Patent: May 7, 2019

(54) CONTINUOUS AUTOFOCUSING EYEWEAR USING STRUCTURED LIGHT

(71) Applicant: Focure Inc., San Francisco, CA (US)

(72) Inventors: Nebojsa Sabovic, San Francisco, CA (US); Reed Foster, San Francisco, CA (US)

(73) Assignee: Focure Inc., San Francisco, CA (US)

( * ) Notice: Subject to any disclaimer, the term of this patent is extended or adjusted under 35 U.S.C. 154(b) by 17 days.

(21) Appl. No.: 15/342,010

(22) Filed: Nov. 2, 2016

(65) Prior Publication Data

US 2017/0123234 A1  May 4, 2017

Related U.S. Application Data

(60) Provisional application No. 62/249,847, filed on Nov. 2, 2015.

(51) Int. Cl.
*A61B 3/14* (2006.01)
*G02C 7/08* (2006.01)

(52) U.S. Cl.
CPC ............... *G02C 7/083* (2013.01); *A61B 3/14* (2013.01)

(58) Field of Classification Search
CPC .................................. G02C 7/083; A61B 3/14
USPC ..................................................... 351/159.39
See application file for complete search history.

(56) References Cited

U.S. PATENT DOCUMENTS

| | | | |
|---|---|---|---|
| 5,220,361 A | 6/1993 | Lehmer | |
| 5,408,292 A * | 4/1995 | Kumakura | G03B 13/02 348/317 |
| 5,532,784 A * | 7/1996 | Nishimura | G03B 13/02 351/210 |
| 5,861,936 A | 1/1999 | Sorensen | |
| 7,286,753 B2 * | 10/2007 | Yamasaki | G02B 27/017 348/61 |
| 7,600,873 B2 * | 10/2009 | Grundig | A61B 3/0025 351/210 |
| 7,654,668 B2 * | 2/2010 | Neuhann | A61B 3/113 351/205 |
| 8,939,579 B2 | 1/2015 | Agurok | |
| 8,955,973 B2 | 2/2015 | Raffle | |
| 2005/0024586 A1 | 2/2005 | Teiwes | |
| 2007/0279584 A1 | 12/2007 | Howell | |
| 2010/0157178 A1 | 6/2010 | Macnaughton | |

(Continued)

FOREIGN PATENT DOCUMENTS

| | | |
|---|---|---|
| WO | 2017079342 A1 | 5/2017 |
| WO | 2017079343 A1 | 5/2017 |

OTHER PUBLICATIONS

D. Li, et al., "Starburst: A Hybrid Algorithm for Video Based Eye Tracking Combining Feature Based and Model Based Approaches", Proc. of the IEEE Vision for Human Computer Interaction Workshop at CVPR, 2005.

(Continued)

*Primary Examiner* — James R Greece
(74) *Attorney, Agent, or Firm* — Daylight Law, P.C.; Eric Scheuerlein

(57) ABSTRACT

Continuously autofocusing eyeglass systems include focus adjustable lenses and a controller to automatically adjust focus power of the lenses to match the correction needed for each eye at the depth of gaze of a user. Focus depth is determined using an image obtained by illuminating the eyes with a structured light illumination source.

18 Claims, 4 Drawing Sheets

(56) References Cited

U.S. PATENT DOCUMENTS

| | | |
|---|---|---|
| 2012/0127062 A1 | 5/2012 | Bar-zeev |
| 2012/0133891 A1 | 5/2012 | Jiang |
| 2012/0194781 A1* | 8/2012 | Agurok .................. A61B 3/113 351/201 |
| 2013/0286178 A1 | 10/2013 | Lewis |
| 2014/0285905 A1 | 9/2014 | Zhou et al. |
| 2014/0375788 A1 | 12/2014 | Gabara |
| 2015/0185503 A1* | 7/2015 | Tate ........................ G06F 3/013 351/158 |
| 2015/0220779 A1 | 8/2015 | Publicover |
| 2015/0243101 A1 | 8/2015 | Schowengerdt |

OTHER PUBLICATIONS

H. Ren, et al., "Tunable-Focus Flat Liquid Crystal Spherical Lens", Applied Physics Letters, vol. 84, No. 23, pp. 4789-4791, Jun. 7, 2004.
R. Valenti, et al., "Accurate Eye Center Location Through Invariant Isocentric Patterns", IEEE Trans. Pattern Analysis and Machine Intelligence, vol. 34, No. 8, pp. 1785-1798, 2012.
S. Shian, et al., "Tunable Lenses Using Transparent Dielectric Elastomer Actuators", Optics Express, vol. 21, No. 7, pp. 8669-8676, Apr. 8, 2013.
PCT International Preliminary Report on Patentability_PCT/US2016/060174_dated May 8, 2018.
PCT International Preliminary Report on Patentability_PCT/US2016/060175_dated May 8, 2018.
PCT International Search Report_PCT/US2016/060174_dated Mar. 24, 2017.
PCT International Search Report_PCT/US2016/060175_dated Jan. 19, 2017.

* cited by examiner

CONTINUOUS AUTOFOCUSING EYEWEAR USING STRUCTURED LIGHT

CROSS-REFERENCE TO RELATED APPLICATIONS

This application claims benefit of priority of U.S. Provisional Application Ser. No. 62/249,847, filed Nov. 2, 2015, which is incorporated herein by reference in its entirety for all purposes.

BACKGROUND OF THE INVENTION

Presbyopia is an age-related farsightedness condition caused by a loss of elasticity in the lens of the eye. This loss of elasticity decreases an adult's ability to accommodate near objects. Children typically have the ability to accommodate 20 dioptres or focus on any object from 50 mm from their eye to infinity. Most adults, by age 50, can only accommodate 2 dioptres. This loss of ability to accommodate generally results in adults requiring some form of visual correction such as reading glasses to focus on near objects. This means that adults must wear reading glasses to accommodate near objects and then remove them to accommodate far objects. In cases where adults also require glasses to correct nearsightedness (inability to accommodate far objects) they must switch between two sets of glasses depending on the depth of their gaze. This is a cumbersome solution for coping with presbyopia as well as myopia and hyperopia. Users would benefit massively from eyewear that adjusted automatically to accommodate near and far objects without requiring manual input from the user.

Several eyewear products have been developed to help adults accommodate both near and far objects using a couple different kinds of lenses. Adlens offers a pair of glasses that uses manually tunable Alvarez lenses that the user can adjust by twisting a knob on each lens. Pixeloptics developed glasses that allow the user to manually switch between two forms of correction (a farsightedness correction and a nearsightedness correction) by pressing a button. Pixeloptics also made a product that uses an accelerometer to allow the user to manually adjust between near and far prescriptions by moving their head. Eyejusters also produced eyewear that allows the user to manually focus Alvarez lenses. Adlens developed eyewear with a membrane lens for continuous focus accommodation that also requires the user to manually adjust a knob on the glasses in order to focus on near or far objects. None of these technologies allows for automatic continuous focus adjustment, but instead rely on user to engage the focus mechanism.

In order for eyewear to make automatic adjustments to a continuous focus lens, it needs to observe the eye and determine the depth of the user's gaze. The relative positions of the pupils are examples of features of the eye that can be used to determine depth of gaze. Sorensen proposed using a neural network to process reflections from the eye to provide an at least partially in focus image in a display screen. (U.S. Pat. No. 5,861,936) The current disclosure uses cameras and a computer controller to track the pupils and determine the depth of gaze using a technique known as structured light. Gersten proposed the use of structured light to display the edge of the pupil on a corneal topography map. (U.S. Pat. No. 5,214,456) Raffle et al suggests that structured light could be used to detect the direction of someone's gaze in their Google Glass application. (U.S. Pat. No. 8,955,973). The current disclosure is not concerned with the direction of the user's gaze, instead it uses structured light to determine the depth of the user's gaze by comparing structured light scans of both eyes numerous times per second.

SUMMARY OF THE INVENTION

The present disclosure is related to autofocusing eyewear for correcting eye accommodative dysfunctions including, but not limited to, presbyopia, myopia, hyperopia, astigmatism and asthenopia. The eyewear comprises a pupil-tracking structured-light system to determine location of the pupils, a focus-tunable lens and a controller to focus the lens based on the position of the pupils. Whereas prior-art gaze-tracking systems used Purkinje points, (U.S. Pat. No. 8,939,579), which depend on the parameters of the eye that need to be calibrated, the present system is able to look at the features of the eyes themselves to determine the position of the eyes in 3D space and therefore the point at which the eyes converge.

The disclosure helps the conditions where the person needs different focal power (for each eye) for looking at the various distances. For instance, for presbyopia, the correction of the lens is the strongest for short distances. For asthenopia, the user might choose to help the muscles in their eye by doing some correction when looking at short distances for a long while. The disclosure can also be used as traditional glasses and provide a single corrective power, and use the calibration mechanism to customize the degree of correction either once or based on some other input, such as the time of day, or an input provided remotely to the eyewear by a nearby device.

The structured-light system works by illuminating the eye in such a way that at least one pupil edge is present in the illumination. This is usually done by projecting at least one line onto the eye. The projected line is captured by the imaging sensor, such as a CMOS sensor. The projected line appears in the image as a curve due to the shape of the eye. The controller then finds the points on the edge, identified as positions in the image where the intensity makes significant change. From the location of the line in the image, the location of the illuminated part of the eye in 3D space can be calculated. Additionally, the shape of the lens in the eye can be discerned, and from it, the data about the lens's current focal distance. This data can be used to calibrate how much additional focal power the user needs. The behavior of the user's lens can also be used to detect if the current prescription is too high or too low. The imaging sensor and the illumination can operate in the infrared range, so as to not interfere with the operation of the eye.

The controller processes the image to find the position and orientation of both eyes in 3D space and uses these coordinates to find the point at which the eyes converge. The controller then uses this data, together with data provided during calibration, to calculate the desired focal power for the lens. This calculation can be either done piecewise, by calculating the angles of both pupils, then uses geometrical relationships to calculate the distance at which gaze lines intersect (the actual viewing depth will depend on the location of the user's fovea centralis), and applying the focal power associated with that distance; or directly, by mapping pupil angles to focal powers. This and any other required mappings and parameters can either be discovered during device operation by looking at the lens feedback or be obtained in the calibration phase, which can either happen before the device is used, or can be incorporated in the regular usage by utilizing user feedback.

The lens is any focus-tunable lens, such as an electromechanical lens (which use electrical motors or electroactive polymers to move or reshape solid, flexible or Alvarez lens) or liquid-crystal lens. An Alvarez lens is known in the art and refers to lenses comprised of two wave-shaped polycarbonate plates that are able to glide across one another. The power of each lens can be adjusted to the desired correction by causing the lenses to glide to the appropriate relative position.

Certain exemplary embodiments utilize an elastomer-liquid lens system which makes use of an inline, transparent electroactive polymer actuator, including a passive membrane, a dielectric elastomer actuator membrane, and a clear liquid. The electroactive membrane is a transparent dielectric elastomer coated with transparent compliant electrodes on both sides. In certain embodiments the dielectric elastomer can be a commercially available acrylic elastomer and the electrodes are single walled carbon nanotube. (Shian et al., *Optics Express*, Vol 21 No. 7, pp 8669-8676, 8 Apr. 2013) The focal length and the numerical aperture of the lens in the rest state are determined by both the refractive index of the liquid and the extent of the membrane bulging. The latter is controlled by the volume of the liquid placed in inside the cavity; more liquid reduces the focal length and increases the numerical aperture of the lens. The focal length of the lens can be designed to increase or decrease upon actuation depending on the location of the electroactive membrane, i.e., as the larger or smaller diameter membrane, respectively.

Tunable focus flat liquid crystal spherical lenses can also be used in certain embodiments. An example of such a lens is a tunable-focus spherical lens using two flat substrates and inhomogeneous electric field over a homogeneous liquid crystal layer as described by Ren et al., Applied Physics Letters, Vol 84, No. 23, pp 4789-4791, 7 Jun. 2004. The top flat substrate has an imbedded spherical indium-tin-oxide electrode and the bottom has a planar ITO electrode on its inner surface. The inhomogeneous electric field generates a centrosymmetric gradient refractive index profile within the LC layer which causes the focusing behavior. The focal length of the LC lens can be tuned continuously from infinity to 0.6 m by the applied voltage. Any other appropriate lens systems known in the art are contemplated by the present disclosure. The lens of any of the described systems can also include a fixed lens, such as an astigmatism-correcting lens.

In addition to auto-focusing eyeglasses, the current disclosure is also useful for screen gaze tracking to identity the position on a screen at which a person looking, virtual or augmented reality, for tracking position and/or depth of gaze, eye typing, surgical applications such as tracking eyes during surgery and medical testing for eye abnormalities and prescription determination, among others that would be apparent to persons of skill in this art.

DESCRIPTION OF PREFERRED EMBODIMENTS

Figure 1:
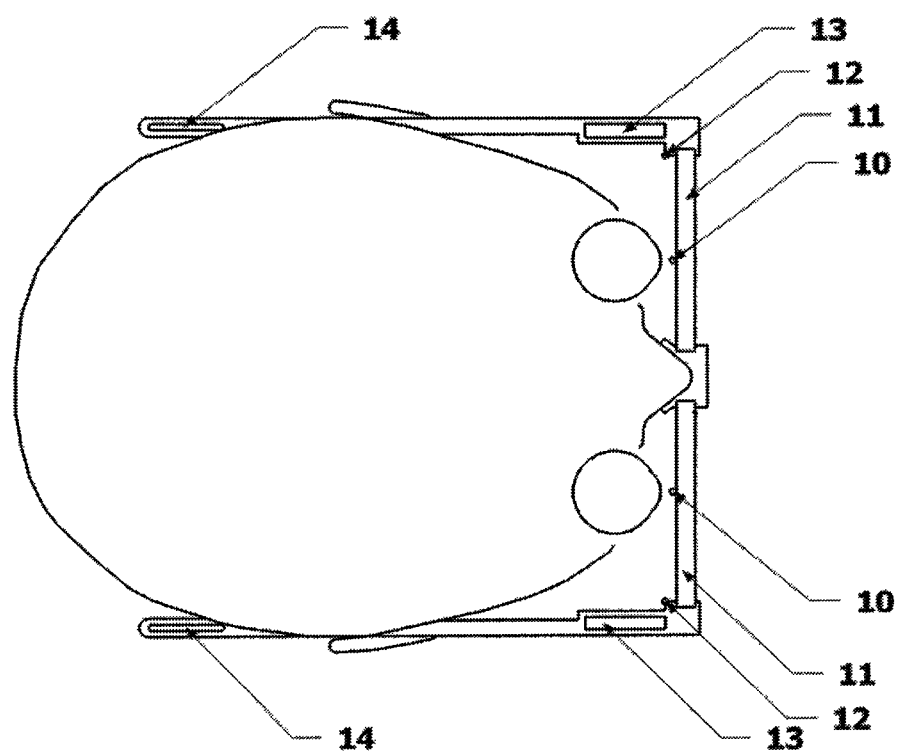
FIG. 1 is a schematic drawing of the current disclosure comprising: imaging subsystem 10, lenses subsystem 11, illumination subsystem 12, controller subsystem 13, battery subsystem 14 and user's eyes, nose and head.

FIG. 1 a schematics diagram showing the various components of the autofocusing eyewear. In this diagram, there are two CMOS sensors forming the imaging subsystem 10, two variable-power lenses forming the lenses subsystem 11, two IR LED lights forming the illumination subsystem 12, controller electronics forming the controller subsystem 13 and the battery subsystem 14 which powers all the other subsystems. These subsystems 10, 11, 12, 13 and 14 are all mounted on an eyeglass frame.

The imaging subsystem 10 is connected to the controller subsystem 13 and provides the image of the eye to be used for determining the depth of gaze. The lens subsystem 11 is connected to and controlled by the controller subsystem 13 and its role is to change the focus of the lens subsystem 11 in accordance with user's depth of gaze. The illumination subsystem 12 is connected to and controlled by the controller subsystem 13. The controller subsystem 13 is responsible for processing the imaging subsystem 10 inputs and controlling the lenses subsystem 11 and illumination subsystem 12. The battery subsystem 14 is connected to all the other subsystems 10, 11, 12 and 13.

Figure 2:
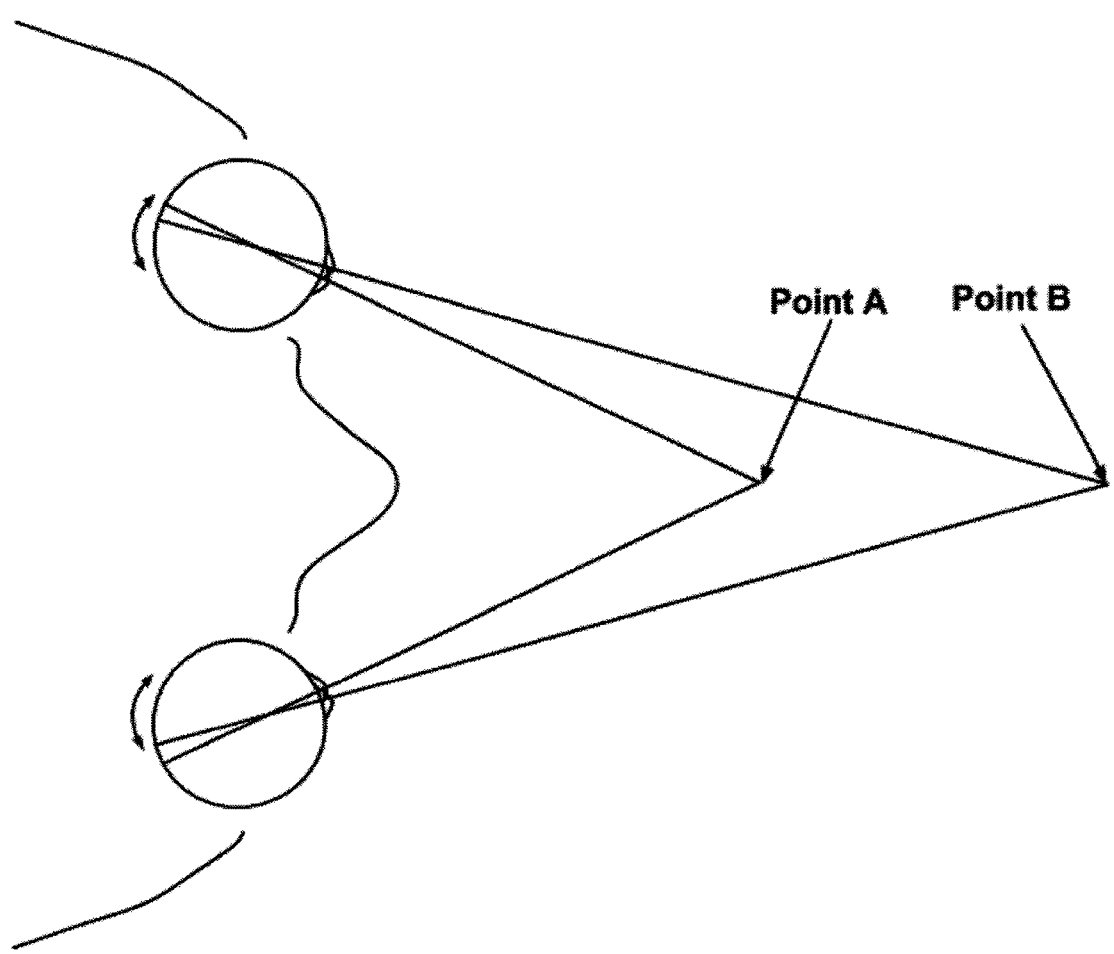
FIG. 2 is a schematic drawing illustrating the function of the imaging subsystem 10 at two different depths of the user's gaze at point A and point B.

The method of operation is based on the following observation. When the user looks at a point A, the eyes rotate so that the two lines originating in each eye's fovea centralis and going through the pupils intersect at that point A. FIG. 2 shows that the angle of the eyes uniquely determines the point A that the user is looking at. Also shown on FIG. 2 is the fact that the eye is not a perfect sphere, but has a deformation where the pupil is. By imaging the surface of the eye, both the parameters of the sphere (namely the center of the eye) and the location of the pupil can be determined.

Figure 3:
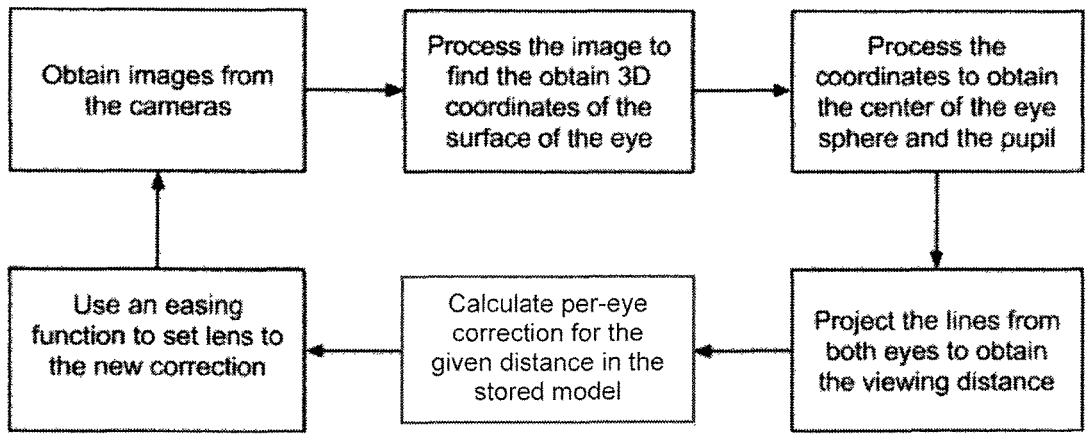
FIG. 3 is the sequence of steps that the eyewear executes in order to detect the gaze depth and adjust the focal power of the lenses.
Figure 4:
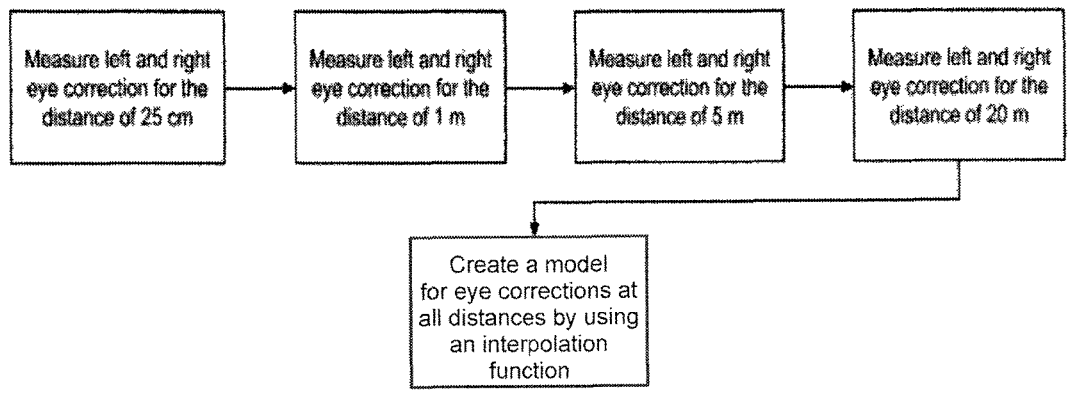
FIG. 4 shows the sequence of steps executed in an example calibration stage before the device can be used.
Figure 5:
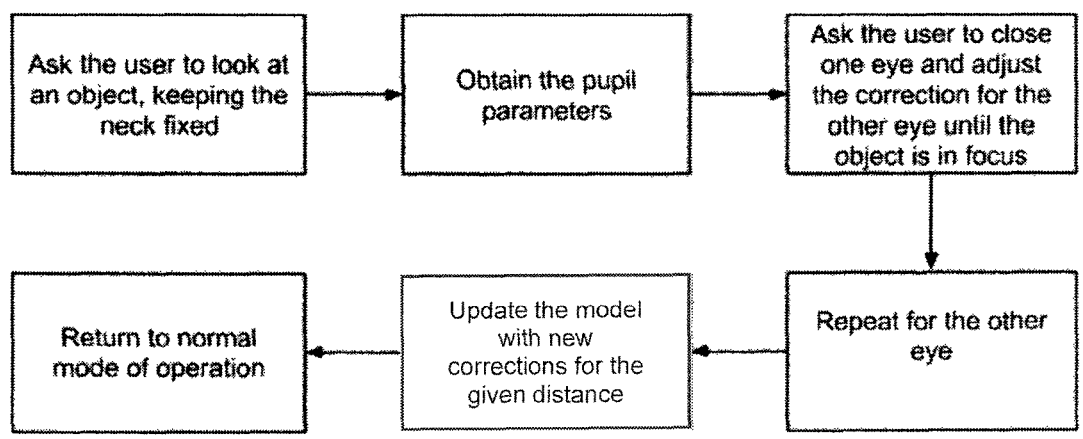
FIG. 5 shows the sequence of steps executed in incremental calibration.

The controller 13 continuously runs a loop shown on schematic diagram on FIG. 3 fifty times per second to determine the depth of the user's gaze and focus the lenses 11 accordingly. To focus the lenses 11, one needs to know the focal power needed by the user at each distance. In this example calibration method, one would also ask the user to enter the focal power required for each of the predetermined distances. This produces a mappings h and $p_R$ of focal powers from the distance d:

$$p_L, p_L(d)$$

$$p_R p_R(d)$$

Certain embodiment can also use incremental calibration. The autofocusing eyewear has a BLUETOOTH® connection which is used with a smartphone or a computer to initiate calibration mode. Whenever the user sees an object that is not in focus, the user enters the calibration mode. The user looks at the object that is not in focus, and uses the smartphone or the computer to adjust the correction for the left and right eye until the object is in focus. This adds a point in each of the mappings h and $p_R$, improving the accuracy of the eyewear.

Once the device is calibrated and the functions $p_L$ and $P_R$ are known, the device is able to plug in the values for the pupil location and obtain the desired corrective power for each lens 11 for the depth of user's current gaze. The controller subsystem 13 repeats the process many times per second, and directs the lenses subsystem 11 to change the focal power to the desired corrective power. In certain embodiments an easing function is used to minimize focusing jitter.

Yet another embodiment can calibrate without user input by using the data about the lenses' thickness which is obtained by 3D imaging of the eye. When the device detects that the user's lenses in the eye are growing in thickness and thereby increasing the prescription it can be deduced that the current prescription is not enough, and the device updates its parameters to add more focal power at the given distance. Similarly, when the device detects that the lenses are shrinking in thickness, the device updates the parameters to add less focal power at that distance. This embodiment can self-calibrate and function without any user interaction.

All of the apparatus, components and methods disclosed and claimed herein can be made and used without undue experimentation in light of the present disclosure. While the apparatus, components and methods of this invention have been described in terms of preferred embodiments, it will be apparent to those of skill in the art that variations may be applied to the construction or components described herein without departing from the concept, spirit and scope of the invention. All such similar substitutes and modifications apparent to those skilled in the art are deemed to be within the spirit, scope and concept of the invention as defined by the appended claims.

The invention claimed is:

1. A process for autofocusing eyewear, comprising the steps of:
   (a) providing images of the eyes of a wearer of the eyewear to a processor;
   (b) processing the images to obtain three-dimensional coordinates of the center of the eye spheres;
   (c) processing the images to obtain three-dimensional coordinates of the pupils of the eyes;
   (d) determining a viewing distance by:
      projecting, using the three-dimensional coordinates of the center of the eye spheres and the three-dimensional coordinates of the pupils of the eyes, a line extending from within each eye through the pupil of each eye; and
      determining a point at which the lines from each eye intersect, wherein the point is at the viewing distance;
   (e) comparing the viewing distance to a model stored in the controller to obtain a correction for each eye at the determined viewing distance; and
   (f) setting each lens of the eyewear to the correction for each eye for the determined viewing distance.

2. The method of claim 1, wherein step (a) comprises projecting at least one line onto the eye wherein the image of the line is curved due to the curved surface of the eye.

3. The method of claim 1, wherein the images are captured with a camera located on the eyewear.

4. The method of claim 1, wherein the images are captured with a plurality of cameras for each eye located on the eyewear.

5. The method of claim 1, wherein step (f) is repeated at intervals of at least ⅕ of a second.

6. The method of claim 5, wherein step (f) is repeated at intervals of up to 1/200 of a second.

7. The method of claim 1, wherein the model is created by determining left and right eye correction at a plurality of distances and creating a model of all distances using an interpolation function.

8. The method of claim 1, wherein the lenses are electromechanical focus tunable lenses.

9. The method of claim 1, wherein the lenses are Alvarez focus tunable lenses.

10. The method of claim 1, wherein the lenses are focus tunable liquid crystal lenses.

11. The method of claim 2, wherein the line is projected using an infra-red light emitting diode.

12. The method in claim 1, wherein determining the viewing distance comprises: projecting the lines from the fovea centralis of each eye through the pupil of each eye.

13. The method of claim 1, wherein the thickness of the eye lens is obtained from the surface coordinates and wherein the model also includes the thickness of the eye lens.

14. The method in claim 1, further comprising:
   illuminating the eyes using a structured light system, wherein the structure light illumination system is located on the eyewear;
   wherein the images of the eyes include a structured light pattern projected by the structured light illumination system; and
   wherein the pattern is used to obtain the three-dimensional coordinates of the centers of the eye spheres.

15. The method in claim 1, wherein determining the viewing distance comprises: projecting the lines from the center of each eye through the pupil of each eye.

16. An autofocusing eyeglass system comprising:
   an eyeglass frame;
   two variable power lenses contained in the eyeglass frame;
   two sensors attached to the eyeglass frame, each adapted to capture an image of an eye of a user;
   two illumination sources attached to the eyeglass frame, each adapted to illuminate an eye of the use;
   a controller attached to the eyeglass frame and electronically connected to the two variable power lenses, the two sensors and the two illumination sources; and
   a battery attached to the eyeglass frame and connected to the controller;
   wherein the controller is adapted to:
      signal the illumination sources to illuminate the eyes;
      receive images of the illuminated eyes from the sensors;
      process the images to obtain three-dimensional coordinates of the center of the eye spheres;
      process the images to obtain three-dimensional coordinates of the pupils of the eyes;
      determine a viewing distance by:
         projecting, using the three-dimensional coordinates of the center of the eye spheres and the three-dimensional coordinates of the pupils of the eyes, a line extending from within each eye through the pupil of each eye; and
         determining a point at which the lines from each eye intersect, wherein the point is at the viewing distance;
      compare the viewing distance to a model stored in the controller to obtain a correction for each eye at the determined viewing distance; and
      set each lens of the eyewear to the correction for each eye for the determined viewing distance.

17. The eyeglass system of claim 16, wherein the illumination sources are infra-red light emitting diodes.

18. The eyeglass system of claim 16, wherein the controller is further adapted to receive manual or wireless feedback to adjust the predetermined corrections at one or more depths of gaze.

* * * * *